(12) United States Patent
Halley et al.

(10) Patent No.: US 10,307,270 B2
(45) Date of Patent: Jun. 4, 2019

(54) BREAST PROSTHESES WITH PHASE CHANGE MATERIAL

(71) Applicants: Robert Halley, Atlanta, GA (US); Amanda Wollnick, Doraville, GA (US); Joachim Rechenberg, Nussdorf am Inn (DE)

(72) Inventors: Robert Halley, Atlanta, GA (US); Amanda Wollnick, Doraville, GA (US); Joachim Rechenberg, Nussdorf am Inn (DE)

(73) Assignee: American Breast Care, LP, Marietta, GA (US)

( * ) Notice: Subject to any disclaimer, the term of this patent is extended or adjusted under 35 U.S.C. 154(b) by 168 days.

(21) Appl. No.: 15/628,761

(22) Filed: Jun. 21, 2017

(65) Prior Publication Data

US 2017/0367850 A1    Dec. 28, 2017

Related U.S. Application Data

(60) Provisional application No. 62/353,861, filed on Jun. 23, 2016.

(51) Int. Cl.
*A61F 2/12* (2006.01)
*A61F 2/52* (2006.01)
*A61F 2/30* (2006.01)

(52) U.S. Cl.
CPC ...... *A61F 2/52* (2013.01); *A61F 2002/30088* (2013.01); *A61F 2210/008* (2013.01); *A61F 2240/001* (2013.01); *A61F 2250/0014* (2013.01)

(58) Field of Classification Search
CPC ... A61F 2/12; A61F 2/52; A41C 3/146; A41C 3/148

USPC ......................................................... 623/7–8
See application file for complete search history.

(56) References Cited

U.S. PATENT DOCUMENTS

| 4,247,351 A | | 1/1981 | Rechenberg | |
|---|---|---|---|---|
| 5,246,454 A | * | 9/1993 | Peterson | A61F 2/12 623/7 |
| 5,534,023 A | * | 7/1996 | Henley | A61F 2/12 623/7 |
| 6,015,332 A | * | 1/2000 | Lee | A41C 3/144 450/38 |
| 6,544,287 B1 | * | 4/2003 | Johnson | A61F 2/12 623/23.72 |

(Continued)

FOREIGN PATENT DOCUMENTS

| WO | 99/25536 | 5/1999 |
|---|---|---|
| WO | 2019/091720 A1 | 6/2013 |

*Primary Examiner* — Suzette J Gherbi
(74) *Attorney, Agent, or Firm* — Bryan W. Bockhop; Bockhop Intellectual Property Law, LLC

(57) ABSTRACT

In a method of making a breast prosthesis for use by a wearer having a body temperature, a plurality of dissolvable beads is placed into an open back of a breast-shaped mold. The open back of the mold is sealed. A suspension of an uncured silicone rubber liquid and a plurality of phase change material pellets is injected into the mold around the beads. The uncured silicone rubber is allowed to cure, thereby forming a breast shape. The phase change material has a latent heat of fusion at a melting point so as to remove heat from the wearer when the body temperature is at least at the melting point. The breast shape is removed from the mold and the dissolvable beads are dissolved from the breast shape.

17 Claims, 4 Drawing Sheets

(56) References Cited

U.S. PATENT DOCUMENTS

| | | | |
|---|---|---|---|
| 6,679,912 B2 | 1/2004 | Stelter | |
| 6,818,673 B2 | 11/2004 | Ferguson | |
| 8,372,423 B2 * | 2/2013 | Marshall | A61L 27/56 |
| | | | 424/400 |
| 8,409,280 B2 * | 4/2013 | Stelter | A61F 2/52 |
| | | | 623/8 |
| 2004/0176841 A1 | 9/2004 | Ferguson | |
| 2008/0181981 A1 * | 7/2008 | Schuessler | A61B 17/12099 |
| | | | 425/447 |
| 2009/0276043 A1 * | 11/2009 | Bowman | A61F 2/52 |
| | | | 623/7 |
| 2010/0023123 A1 * | 1/2010 | Laghi | A61F 2/5046 |
| | | | 623/7 |
| 2015/0245902 A1 * | 9/2015 | Becker | A61F 2/12 |
| | | | 623/8 |
| 2018/0092737 A1 * | 4/2018 | Barere | A61L 27/18 |
| 2019/0038397 A1 * | 2/2019 | Becker | A61F 2/0059 |

* cited by examiner

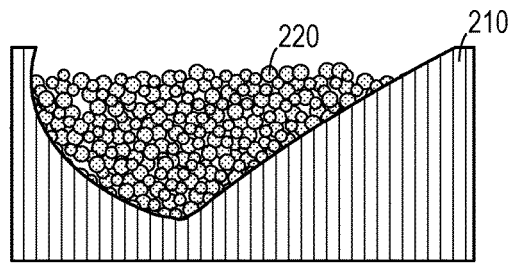
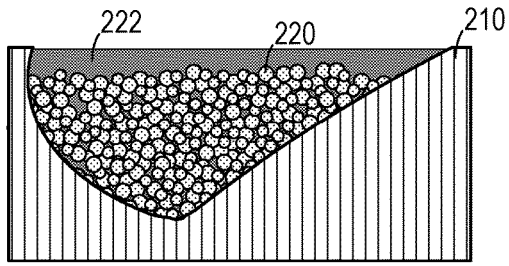
FIG. 2A        FIG. 2B
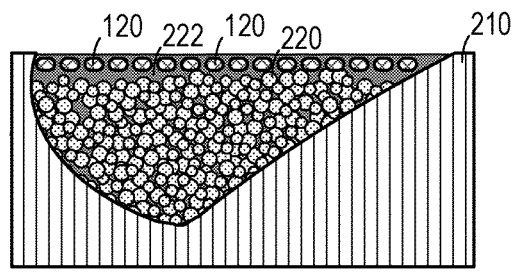
FIG. 2C
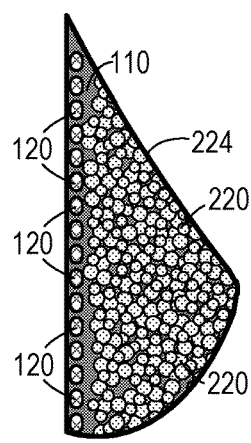
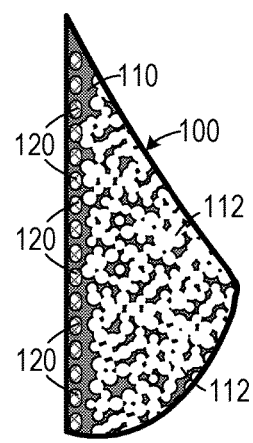
FIG. 2D        FIG. 2E

BREAST PROSTHESES WITH PHASE CHANGE MATERIAL

CROSS-REFERENCE TO RELATED APPLICATION(S)

This application claims the benefit of U.S. Provisional Patent Application Ser. No. 62/353,861, filed Jun. 23, 2016, the entirety of which is hereby incorporated herein by reference.

BACKGROUND OF THE INVENTION

1. Field of the Invention

The present invention relates to breast prostheses and, more specifically, a breast prosthesis that includes a phase change material.

2. Description of the Related Art

A major complaint when wearing a breast prosthesis is heat being trapped behind the prosthesis leading to discomfort for the wearer. In traditional gel-type breast prostheses, several strategies have been developed to alleviate this problem. One such strategy involves adding a phase change material (PCM) to the gel. The PCM retains latent heat as it melts and, thereby maintains its temperature during its phase transition from solid phase to liquid phase. The PCM is chosen so as to have a melting point corresponding to the body temperature of the user so that temperature increase in the prosthesis is checked for a period after the user begins wearing it. However, gel-type breast prostheses require a film between the wearer and the gel. As a result, there is no direct contact between the user's chest and the PCM, thereby reducing the heat transfer efficiency of the prosthesis. Also, gel-type breast prostheses tend not to have a natural shape and do not lend themselves to the addition of desirable cosmetic features, such as veins and freckles, that result in a more natural look.

Custom rubber-type prostheses do have a natural shape and cosmetic features can be added to them. However, in custom rubber-type prostheses, heat buildup is a common concern for wearers. Such custom prostheses often employ a spongy material that acts as an insulator. As a result, wearing such prostheses can become uncomfortable after a limited amount of time.

Therefore, there is a need for custom rubber-type breast prosthesis that manages heat buildup.

SUMMARY OF THE INVENTION

The disadvantages of the prior art are overcome by the present invention which, in one aspect, is a method of making a breast prosthesis for use by a wearer having a body temperature, in which a plurality of dissolvable beads is placed into an open back of a breast-shaped mold. The open back of the mold is sealed. A suspension of an uncured silicone rubber liquid and a plurality of phase change material pellets is injected into the mold around the beads. The uncured silicone rubber is allowed to cure, thereby forming a breast shape. The phase change material has a latent heat of fusion at a melting point so as to remove heat from the wearer when the body temperature is at least at the melting point. The breast shape is removed from the mold and the dissolvable beads are dissolved from the breast shape.

In another aspect, the invention is a breast prosthesis for use by a wearer who has a body temperature. A silicone rubber body portion has a shape corresponding to a human breast. The silicone rubber body portion defines a plurality of gas-filled voids therein. A phase change material is suspended within the silicone rubber of the body portion. The phase change material has a latent heat of fusion at a melting point so as to remove heat from the wearer when the body temperature is at least at the melting point.

In yet another aspect, the invention is an external breast prosthesis for use by a wearer who has a body temperature. A silicone rubber body portion has a shape corresponding to a human breast and defines a plurality of gas-filled voids therein. A paraffin phase change material is suspended within the silicone rubber. The paraffin phase change material has a predetermined number of carbon atoms per molecule so as to have a latent heat of fusion at a melting point so as to remove heat from the wearer when the body temperature is at least at the melting point. An outer skin layer is disposed about the silicone rubber body portion.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

BRIEF DESCRIPTION OF THE FIGURES OF THE DRAWINGS

FIG. 2A-2E is a series of schematic diagrams demonstrating one method of making a breast prosthesis.

DETAILED DESCRIPTION OF THE INVENTION

Figure 1:
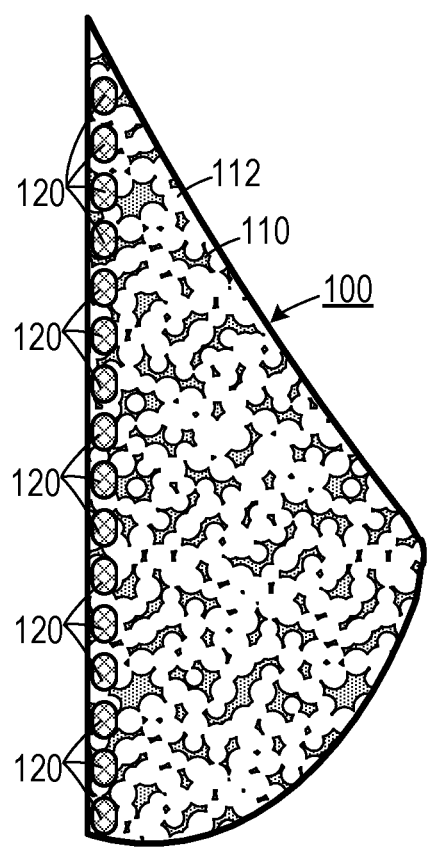
FIG. 1 is a schematic diagram showing a side cross-sectional view of one embodiment of a breast prosthesis.
Figure 3A:
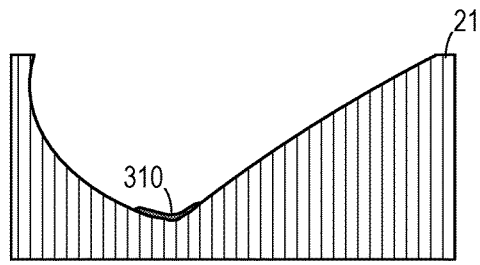
FIGS. 3A-3F is a series of schematic diagrams demonstrating a second method of making a breast prosthesis.
Figure 3B:
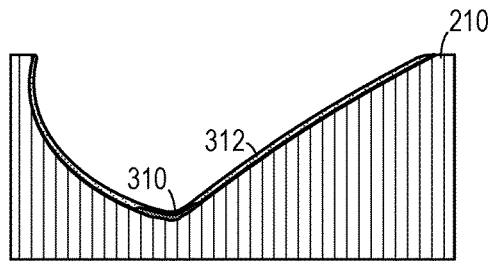
Figure 3C:
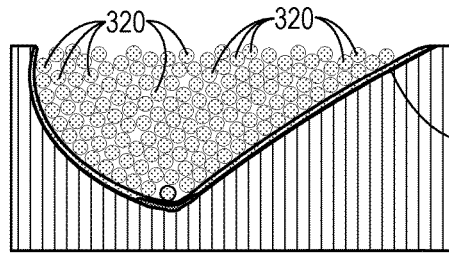
Figure 3D:
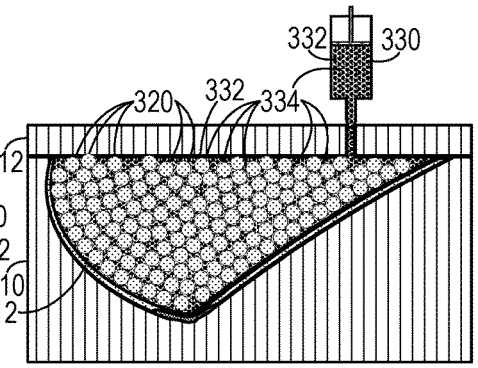
Figure 3E:
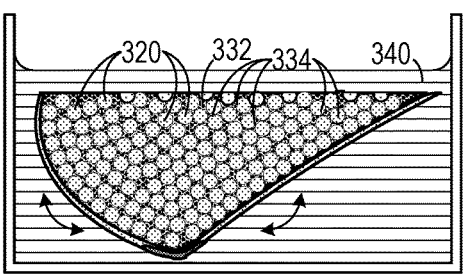
Figure 3F:
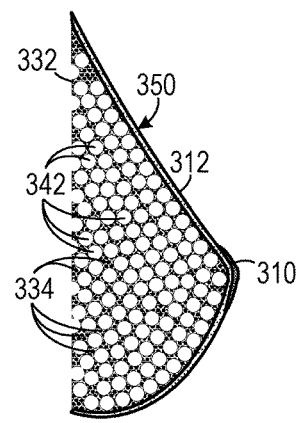

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIG. 1, one representative embodiment of a breast prosthesis 100 includes a rubber matrix 110 (that includes, for example, a silicone rubber) that suspends a plurality of air voids 112, or other lightweight inclusions, in the shape of a human breast.

A phase change material (PCM) is embedded in the rubber matrix 110. In one embodiment, the PCM can be in the form of pellets or capsules. In one representative embodiment, the PCM can include paraffin in which the average molecule has 20 or fewer carbon atoms. A paraffin with 20 carbon atoms per molecule would have a melting point of about 98° F. (which is the average body temperature of a person), whereas a paraffin with 14 carbon atoms per molecule would have a melting point of about 42° F. Thus, the melting point can be tuned to a specific desired temperature. In certain embodiments, PCMs of a range of melting points can be used so that they begin absorbing heat at different temperatures.

As shown in FIG. 2A, in one method of making a breast prosthesis, a plurality of beads 220 are poured into a mold 210 having a shape complimentary to that of a human breast. The beads could include a water-soluble substance such as common table sugar or salt. (In an alternate embodiment, the beads could include a lightweight non-soluble substance, such as expanded micro-spheres.) As shown in FIG. 2B, an uncured silicone rubber 222 is added to the beads 220. As shown in FIG. 2C, PCM pellets or capsules 120 are added to the uncured silicone rubber 222. The uncured silicone rubber 222 is cured and the cured breast form 224 is removed from the mold 210, as shown in FIG. 2D. As shown in FIG. 2E, the beads 220 are dissolved away from the breast form 224, leaving air voids 112 in the cured rubber matrix 110, resulting in the final breast prosthesis 100.

As shown in FIGS. 3A-3F, in one method of making a breast prosthesis, a liquid silicone rubber precursor that includes a pigment having the color of a natural nipple is applied to a portion of a mold 210 corresponding to the location of a nipple in the resulting prosthesis and is allowed to cure, thereby generating an image of a nipple 310. Once cured, a front skin layer 312 (or several layers in some embodiments) is applied to the mold and allowed to cure. The thickness of the layer(s) of silicone rubber and the firmness of the silicone rubber are chosen to have a feel similar to human skin. The skin layer 312 can have pigments and other additives to mimic the appearance and texture of skin. The skin layer 312 is formed to the shape of a breast by the mold 210, which can be either a custom shape from an individual measurement or a more generic shaped breast. Additional features, such as images of veins and freckles can be included in the skin layer 312.

Dissolvable beads 320 (such as sugar beads or salt beads) are placed into the mold 210 and a back 312 is affixed to the mold 210. In one embodiment, sugar beads (also referred to as "sugar pellets" and "sugar pearls") of the type commonly known to the baking and pharmaceutical industries are used. In one embodiment, the sugar beads have a diameter of about 2 mm, in other embodiments they range in diameter from 1 mm to 4 mm. It has been found that sugar beads tend to dissolve more quickly than salt beads.

A suspension of silicon liquid rubber precursor 332 and phase change material pellets 334 (such a paraffin pellets) is injected into the mold 210 around the dissolvable beads 320 with a viscous liquid injecting device, such as an air gun-type viscous liquid pump. (The silicone rubber precursors for the nipple portion, the skin layer and the suspension can include, for example, Dragon Skin series or Ecoflex series two-part silicon available from Smooth-On, Inc., 5600 Lower Macungie Road, Macungie, Pa. 18062.) The silicone curing time typically varies between 30 minutes to four hours, depending upon the specific silicone formulation used. Typically, the silicone for nipple 310 and skin layer 312 is harder than fill silicone 332.

Once the silicone rubber 332 has cured, then the prosthesis 350 is placed in a solvent 340 (which could include water) to allow the dissolvable beads 320 to dissolve from the prosthesis, leaving air-filled voids 342 surrounded by a matrix of silicone rubber 332 and phase change material pellets 334. The dissolution can be helped by gently agitating and squeezing the prosthesis 350 during the dissolution period. The dissolution time depends upon the size of the prosthesis and typically takes between 10 minutes to several days to complete.

In most embodiments, the front of the mold 210 will have the shape of a breast as it would be held in a bra cup. The back 312 of the mold will have the shape of a chest. The shape can be produced to match a specific patient or can be a general shape. The mold 210 can be made of any typical mold making material including aluminum or tooling board.

Figure 4:
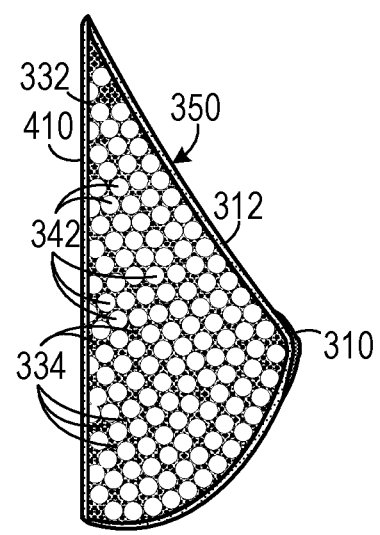
FIG. 4 is a schematic diagram showing a side cross-sectional view of one alternate embodiment of a breast prosthesis.

As shorn in FIG. 4, a back skin layer 410 may be applied to part or all of the back of the prosthesis 350. The skin layer 410 can also include phase change material pellets.

In one embodiment, phase change material pellets 334 can include pellets having different latent heats of fusion (and correspondingly different melting points) so that they sequester heat at different temperatures. For example, some of the pellets could be chosen to begin melting at 95° F., while others would begin melting at 85° F. and still others would begin melting at 75° F., which would allow for heat sequestration in various temperatures. (The typical body temperature of a wearer would be about 97.9° F., so this temperature range would provide rapid cooling as the 75° F. beads melted, followed by gradual cooling as the other beads melted.) In one embodiment, a phase change material with a transition temperature substantially below body temp can be used. For example, in an embodiment employing a phase change material with a transition temperature of 75° F., the prosthesis could be cooled in a refrigerator prior to being worn. The lower transition temperature would allow for the form to remain at a cooler temperature, which could be useful for a patient with sensitive or damaged skin. Also, the silicon rubber matrix material can be added in layers, which could contain different phase change materials (e.g., phase change materials that melt at different temperatures and also phase change material pellets of different sizes).

In one embodiment, dissolvable beads are not used and the silicone rubber liquid includes chemical foaming agents, which result in the formation of gas-filled voids in the silicone rubber of the prosthesis as the silicone rubber cures.

The silicone rubber with PCM and gaseous voids of the present invention has several advantages over existing systems. For example, the present invention has an advantage over gel systems in that no film is necessary to contain a gel so that the PCM will be in material that can be directly touching the patient's chest, thereby improving heat transfer. The silicone rubber used creates a more realistic looking prosthesis, which can including the possibility of such cosmetic features as the images of nipple, veins, freckles, etc. The silicone rubber employed allows for more complex shapes. The silicone rubber allows for lighter breast prostheses than gel prostheses. Gel prostheses can have reduced densities in the 0.55 to 0.70 g/ml range. The present invention, on the other hand, can product a prostheses with a density of approx. 0.40 g/ml. This results in a significantly more comfortable wearing experience.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A breast prosthesis for use by a wearer who has a body temperature, comprising:
    (a) a silicone rubber body portion having a shape corresponding to a human breast, the silicone rubber body portion defining a plurality of gas-filled voids therein; and
    (b) a phase change material suspended within the silicone rubber of the body portion, the phase change material having a latent heat of fusion at a melting point so as to remove heat from the wearer when the body temperature is at least at the melting point, wherein the phase change material includes:
        (i) phase change material pellets of a first type which have a first latent heat of fusion at a first melting point; and
        (ii) phase change material pellets of a second type which have a second latent heat of fusion, different from the first latent heat of fusion, at a second melting point, different from the first melting point.

2. A breast prosthesis for use by a wearer who has a body temperature, comprising:
    (a) a silicone rubber body portion having a shape corresponding to a human breast, the silicone rubber body portion defining a plurality of gas-filled voids therein; and
    (b) a phase change material suspended within the silicone rubber of the body portion, the phase change material having a latent heat of fusion at a melting point so as to remove heat from the wearer when the body temperature is at least at the melting point, wherein the phase change material comprises a paraffin with a predetermined number of carbon atoms per molecule and wherein the predetermined number of carbon atoms per molecule consists of a range of 14 to 20 carbon atoms per molecule.

3. A breast prosthesis for use by a wearer who has a body temperature, comprising:
    (a) a silicone rubber body portion having a shape corresponding to a human breast, the silicone rubber body portion defining a plurality of gas-filled voids therein; and wherein the body portion comprises an outer silicone rubber skin layer, wherein the skin layer comprises a nipple-like structure that includes silicone rubber and has a shape and a pigmentation corresponding to a natural nipple; and
    (b) a phase change material suspended within the silicone rubber of the body portion, the phase change material having a latent heat of fusion at a melting point so as to remove heat from the wearer when the body temperature is at least at the melting point.

4. A breast prosthesis for use by a wearer who has a body temperature, comprising:
    (a) a silicone rubber body portion having a shape corresponding to a human breast, the silicone rubber body portion defining a plurality of gas-filled voids therein; and
    (b) a phase change material suspended within the silicone rubber of the body portion, the phase change material having a latent heat of fusion at a melting point in a range of between 75° F. to 98° F. so as to change phase from solid to liquid and thereby remove heat from the wearer when the body temperature is at least at the melting point.

5. The breast prosthesis of claim 4, wherein the phase change material comprises a paraffin.

6. The breast prosthesis of claim 4, wherein the phase change material includes:
    (a) phase change material pellets of a first type which have a first latent heat of fusion at a first melting point; and
    (b) phase change material pellets of a second type which have a second latent heat of fusion, different from the first latent heat of fusion, at a second melting point, different from the first melting point.

7. The breast prosthesis of claim 4, wherein the body portion comprises an outer silicone rubber skin layer.

8. The breast prosthesis of claim 7, wherein the skin layer comprises a nipple-like structure that includes silicone rubber and has a shape and a pigmentation corresponding to a natural nipple.

9. A breast prosthesis for use by a wearer who has a body temperature, comprising:
    (a) a silicone rubber body portion having a shape corresponding to a human breast, the silicone rubber body portion defining a plurality of interconnected air-filled voids therein; and
    (b) a phase change material suspended within the silicone rubber of the body portion.

10. The breast prosthesis of claim 9, wherein the a phase change material has a latent heat of fusion at a melting point in a range of between 75° F. to 98° F. so as to change phase from solid to liquid and thereby remove heat from the wearer when the body temperature is at least at the melting point.

11. The breast prosthesis of claim 9, wherein the phase change material comprises a paraffin.

12. The breast prosthesis of claim 9, wherein the body portion comprises an outer silicone rubber skin layer.

13. The breast prosthesis of claim 12, wherein the skin layer comprises a nipple-like structure that includes silicone rubber and has a shape and a pigmentation corresponding to a natural nipple.

14. The breast prosthesis of claim 1, wherein the body portion comprises an outer silicone rubber skin layer, the skin layer including a nipple-like structure that includes silicone rubber and has a shape and a pigmentation corresponding to a natural nipple.

15. The breast prosthesis of claim 1, wherein the phase change material comprises a paraffin with a predetermined number of carbon atoms per molecule and wherein the predetermined number of carbon atoms per molecule consists of a range of 14 to 20 carbon atoms per molecule.

16. The breast prosthesis of claim 3, wherein the a phase change material has a latent heat of fusion at a melting point in a range of between 75° F. to 98° F. so as to change phase from solid to liquid and thereby remove heat from the wearer when the body temperature is at least at the melting point.

17. The breast prosthesis of claim 3, wherein the phase change material comprises a paraffin with a predetermined number of carbon atoms per molecule and wherein the predetermined number of carbon atoms per molecule consists of a range of 14 to 20 carbon atoms per molecule.

* * * * *